United States Patent [19]

Haefliger

[11] Patent Number: 4,791,115

[45] Date of Patent: Dec. 13, 1988

[54] 2,6-DIMETHYL-8α-PIVALOYLAMINO-9,10-DIDEHYDRO-ERGOLINE

[75] Inventor: Walter Haefliger, Langnau, Switzerland

[73] Assignee: Sandoz Ltd., Basel, Switzerland

[21] Appl. No.: 2,055

[22] Filed: Jan. 12, 1987

Related U.S. Application Data

[63] Continuation of Ser. No. 811,079, Dec. 18, 1985, abandoned.

[30] Foreign Application Priority Data

Dec. 24, 1984 [DE] Fed. Rep. of Germany ....... 3447383

[51] Int. Cl.$^4$ .................. A61K 31/48; C07D 457/12
[52] U.S. Cl. ........................................ 514/288; 546/68
[58] Field of Search ......................... 546/68; 514/288

[56] References Cited

U.S. PATENT DOCUMENTS 3,218,323 11/1916 Hofmann et al. ................. 546/68
4,348,391 9/1982 Stütz et al. ...................... 546/68
4,448,392 9/1982 Fehr et al. ....................... 546/68

FOREIGN PATENT DOCUMENTS 622518 4/1981 Switzerland ..................... 546/68
1041862 9/1966 United Kingdom ............... 546/68

OTHER PUBLICATIONS

Salvadi et al., CA 103-32119g.
Cider et al., CA 87-177456a.
Stuetz et al., CA 93-46946m.
Fehr et al., CA 98-54276m.
Stuetz et al., CA 98-198513j.
Haffer et al., CA 99-158703k.
Haefliger, CA 104-130106r.
Stuetz et al., CA 84-165094f.

Primary Examiner—Donald G. Daus
Assistant Examiner—Cecilia Shen
Attorney, Agent, or Firm—Gerald D. Sharkin; Robert S. Honor; Thomas O. McGovern

[57] ABSTRACT

Compounds of formula I

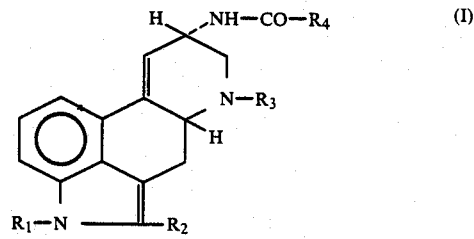

wherein $R_1$ is hydrogen or $C_{1-4}$alkyl, $R_2$ is hydrogen, chlorine, bromine or methyl, $R_3$ is $C_{1-5}$alkyl or $C_{3-5}$alkenyl and $R_4$ is $C_{1-7}$alkyl; $C_{3-7}$cycloalkyl; adamantyl; or optionally substituted phenyl, are useful as neuroleptic agents and PRL secretion inhibitors.

4 Claims, No Drawings

2,6-DIMETHYL-8α-PIVALOYLAMINO-9,10-DIDEHYDRO-ERGOLINE

This is a continuation of application Ser. No. 811,079, filed Dec. 18, 1985, now abandoned.

The present invention relates to novel 8α-acylamino-ergolines, processes for their production, pharmaceutical compositions containing them and their use as pharmaceuticals.

The present invention provides a novel group of 8α-acylamino-ergolines, which have been found to possess especially interesting or advantageous biological activity or profile.

More particularly the present invention relates to compounds of formula I

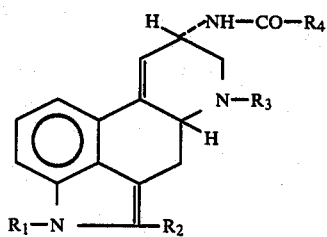

wherein
$R_1$ is hydrogen or $C_{1-4}$alkyl,
$R_2$ is hydrogen, chlorine, bromine or methyl,
$R_3$ is $C_{1-5}$alkyl or $C_{3-5}$alkenyl in which the double bond is not at the carbon atom adjacent to the nitrogen atom, and
$R_4$ is $C_{1-7}$alkyl; $C_{3-7}$cycloalkyl; adamantyl; phenyl; phenyl substituted by one or more members selected from the group consisting of $C_{1-3}$alkyl, $C_{1-3}$alkoxy, $C_{1-3}$alkylthio, trifluoromethyl, hydroxy, nitro, amino and mono- and di-($C_{1-3}$alkyl)-amino; or phenyl fused with a non-aromatic, heterocyclic ring having 5- or 6-ring members including 1 or 2 hetero atoms selected from the group consisting of oxygen and/or sulphur,
with the proviso that when $R_2$ is hydrogen, neither $R_3$ nor $R_4$ is methyl, as well as the acid addition salts thereof.

A preferred group of compounds of formula I are those of formula Ia

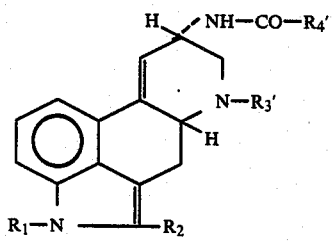

wherein
$R_1$ and $R_2$ have the meanings given for formula I,
$R_3'$ is $C_{2-5}$alkyl or $C_{3-5}$alkenyl in which the double bond is not at the carbon atom adjacent to the nitrogen atom, and
$R_4'$ is (i) $C_{3-7}$alkyl or $C_{3-7}$cycloalkyl; or (ii) phenyl; phenyl substituted by one or two members selected from the group consisting of $C_{1-2}$alkyl, $C_{1-2}$alkoxy, $C1-2$alkylthio, hydroxy and nitro; or phenyl substituted at two adjacent carbon atoms by a divalent residue of formula $—O—CH_2—O—$ or $—Z—(CH_2)_n—$, wherein Z is oxygen or sulphur and n is 2 or 3.

A further preferred group of compounds of formula I are those of formula Ib

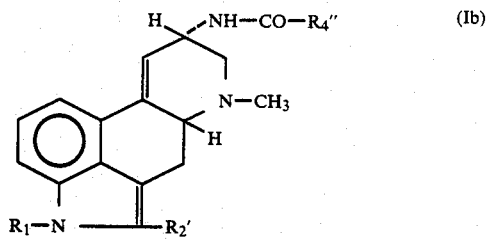

wherein
$R_1$ has the meaning given for formula I,
$R_2'$ is chlorine, bromine or methyl, and
$R_4''$ is $C_{1-7}$alkyl, $C_{3-7}$cycloalkyl or adamantyl.

Alkyl groups and moieties in the compounds of formulae I, Ia or Ib may be straight- or branched-chain.

In formula I $R_2$ is conveniently chlorine, bromine or methyl. $R_3$ is preferably $C_{1-5}$alkyl.

For the above formula Ib, the following significances, as well as combinations thereof, are preferred:
1. $R_1$ is hydrogen or methyl, especially hydrogen.
2. $R_4''$ is $C_{3-7}$alkyl, especially branched-chain $C_{3-7}$alkyl, in particular branched-chain $C_{3-5}$alkyl, most preferably t.butyl.

The present invention also provides a process for the production of the compounds of formula I and their acid addition salts, which process comprises:

(a) reacting a compound of formula II

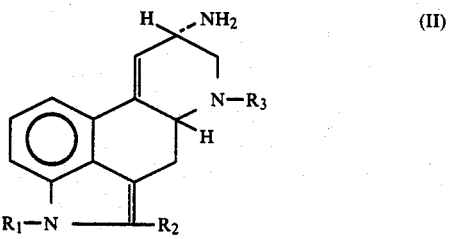

wherein $R_1$, $R_2$ and $R_3$ have the meanings given above with a compound of formula III $$R_4—COOH \qquad (III)$$

wherein $R_4$ has the meaning given above, or a reactive functional derivative thereof;

(b) chlorinating or brominating a compound of formula I wherein $R_2$ is hydrogen to produce the corresponding compound of formula I wherein $R_2$ is chlorine or bromine; or (c) N-($C_{1-4}$alkylating) a compound of formula I wherein $R_1$ is hydrogen to produce a corresponding compound of formula I wherein $R_1$ is $C_{1-4}$alkyl;
and recovering the obtained compound of formula I as such or as an acid addition salt thereof.

Process step (a) may be carried out in accordance with standard procedures. Suitable reactive functional derivatives of the compounds of formula III include e.g. the corresponding acyl halides, in particular chlorides, and imidazolides. Reaction with acyl halides is suitably effected in the presence of a base, such as triethylamine or Hünig-base. Reaction with imidazolides (obtained e.g. by reaction of the compound of formula III with N,N-carbonyldiimidazole) is suitably carried out in an inert solvent such as tetrahydrofuran or ethanol, e.g. at reflux temperature. Suitable is also the condensation of an amino-ergoline with a carboxylic acid in the presence of propanephosphonic acid anhydride.

Process step (b) may also be carried out in accordance with known techniques, using standard chlorinating or brominating agents such as N—Br— or N—Cl-succinimide, sulphuryl chloride or pyrrolidonehydrobromideperbromide. The reaction is conveniently performed in the presence of an inert diluent or solvent such as methylene chloride or tetrahydrofuran.

Process step (c) may be carried out in accordance with known methods for the N-alkylation of indoles, e.g. employing a compound of formula IV $$R_1^1-X \qquad (IV)$$

wherein $R_1^1$ is $C_{1-4}$alkyl and X is a leaving group, e.g. a halogen atom, in particular chlorine, fluorine or bromine atom, or methane- or p-toluene-sulfonyloxy group. The reaction is suitably carried out in the presence of an inert solvent or diluent such as dimethylsulfoxide, preferably in the presence of an acid binding agent such as KOH.

The starting materials of formula II are known or may be produced analogously to the known compounds and in accordance with known procedures. The starting materials for steps (b) and (c) may be prepared in accordance with process step (a).

The compounds of formula I may be recovered from the initially obtained reaction medium as such (i.e. in free base form) or in acid addition salt form e.g. in the form of their pharmaceutically acceptable acid addition salts. Suitable pharmaceutically acceptable acid addition salts include both such salts with inorganic acids, for example the hydrochloride salts, as well as such salts with organic acids, for example the oxalates and maleates.

The following examples are illustrative of the processes for the production of the subject compounds.

EXAMPLE 1

2,6-Dimethyl-8α-pivaloylamino-9,10-didehydro-ergoline

A suspension of 3.38 g 8α-amino-2,6-dimethyl-9,10-didehydro-ergoline in 60 ml $CH_2Cl_2$ and 3.7 ml triethylamine is treated dropwise at 0°–5° (ice bath) with a solution of 1.8 ml pivaloyl chloride in 15 ml $CH_2Cl_2$. The reaction mixture is then stirred overnight at room temperature and then treated with saturated $K_2CO_3$ solution. The organic layer is dried ($Na_2SO_4$) and evaporated. The residue is chromatographed on silica gel using 97:3 $CH_2Cl_2/CH_3OH$. On crystallisation from ether the title compound, m.p. 155° (sintering at 150°) is obtained.

The starting material is obtained as follows:

(a) 2-Methyl-lysergic acid methyl ester

To a suspension of 25 g 2-methyl-lysergic acid in 500 ml $CH_3OH$ are added 253 ml 3.5N $HCl/CH_3OH$. The reaction mixture is then stirred at room temperature for 15 hours, then diluted with 500 ml $CH_3OH$ and stirred 2 days. The mixture is evaporated and partitioned between ethyl acetate and 5% $K_2CO_3$ solution. After drying and evaporating the heading compound is obtained as crystals, which are then rubbed with ether/hexane (1:1), m.p. 154° (sintering 150°).

(b) 2-methyl-isolysergic acid hydrazide 15.9 g hydrazine hydrochloride and 18.4 ml hydrazine hydrate are added under stirring to 22.5 g of the product of step (a) in 20 ml n-propanol and the obtained reaction mixture is heated under reflux for 5 hours. The mixture is concentrated, treated with 500 ml $H_2O$, filtered and washed with $H_2O$ (fraction A). The mother liquor is extracted with ethyl acetate and the extract evaporated. To the residue (7.5 g) are added 100 ml n-propanol and 20 ml triethylamine and the mixture is stirred and heated at reflux. The reaction is followed by thin layer chromatography. After approximately 15 hours when all of the β-product is converted into the 8α-product, $H_2O$ is added and the mixture is filtered. The filter cake is combined with fraction A and recrystallized twice from hot ethanol to afford the heading compound, m.p. 235°–240°, which is the pure α-isomer by NMR.

(c) 8α-Amino-2,6-dimethyl-9,10-didehydro-ergoline 1.4 g sodium nitrite in 5 ml $H_2O$ are added dropwise within 10 minutes under ice-cooling and stirring to 6.8 g of the product of step (b) in 200 ml 0.2N HCl. The reaction mixture is stirred under ice-cooling for 15 minutes and added dropwise unter nitrogen to 100 ml refluxing 0.4N HCl within 15 minutes. Stirring is continued for 10 minutes. The mixture is then cooled, rendered alkaline with saturated $K_2CO_3$ solution and extracted about 7 times with 9:1 $CH_2Cl_2/1\ CH_3OH$, whereby the black residue remains in the aqueous phase. The organic phase is dried ($Na_2SO_4$), evaporated, the resulting foam is chromatographed on silica gel using 80:20:0.7 $CH_2Cl_2/CH_3OH/NH_3$ to afford the heading compound as a brown resin (pure 8α-compound by NMR).

EXAMPLE 2

2-Bromo-6-methyl-8α-pivaloylamino-9,10-didehydro-ergoline

A solution of 1.5 g 6-methyl-8α-pivaloylamino-9,10-didehydro-ergoline in 120 ml dioxane is treated with 960 mg N-bromosuccinimide and the resulting mixture stirred at room temperature overnight The reaction mixture is then evaporated and the residue partitioned between ethyl acetate and 2N $Na_2CO_3$. The organic layers are dried ($Na_2SO_4$), evaporated and chromatographed on 80 g silica gel using 98:2 $CH_2Cl_2/CH_3OH$. Crystallization from ether gives the title compound, m.p. 169°–171°.

The starting material may be obtained as follows:

A suspension of 5.5 g 8α-amino-6-methyl-9,10-didehydro-ergoline in 200 ml $CH_2Cl_2$ is cooled to 0° and treated with 6.44 ml triethylamine followed by dropwise addition of 2.97 ml pivaloyl chloride. The mixture is stirred for 2 hours at room temperature and washed with water. The organic layer is dried ($Na_2SO_4$) and evaporated. The residue is chromatographed on 200 g silica gel using 98:2 $CH_2Cl_2/CH_3OH$ and then crystallized from ether to yield 6-methyl-8α-pivaloylamino-9,10-didehydro-ergoline, m.p. 158°–159°.

EXAMPLE 3

2-Chloro-6-methyl-8α-pivaloylamino-9,10-didehydro-ergoline

A mixture of 2.0 g 6-methyl-8α-pivaloylamino-9,10-didehydro-ergoline, 100 ml $CH_2Cl_2$ and 50 mg silica gel is cooled to 0° and treated dropwise with 0.73 ml sulfurylchloride. The mixture is then stirred for 16 hours at room temperature, and then treated with 2N $Na_2SO_4$ and $CH_2Cl_2$. The organic phase is dried ($Na_2SO_4$), evaporated and chromatographed on 100 g silica gel using 8:2 $CH_2Cl_2/CH_3OH$. The title compound is obtained on crystallisaton from ether, m.p. 157°-160°.

EXAMPLE 4

6-n-Propyl-8α-benzoylamino-9,10-didehydro-ergoline

In manner analogous to that described in Example 1 the title compound is produced.

$^1$H-NMR (360 MHz, DMSO): 0,9 (t, 3H); 1,5 (m, 2H); 2,55-3,35 (m, 6H); 3,35-3,45 (m, 1H); 4,75 (s, 1H, broad); 6,3 (m, 1H); 7,0-7,6 (m, 7H); 7,9 (m, 2H); 8,45 (d, 1H); 10,7 (s, 1H).

The compounds of formula I exhibit pharmacological activity and are therefore indicated for use as pharmaceuticals, e.g. for therapy.

In particular the compounds of formula I especially compounds of formula Ib possess apomorphine antagonistic activity as demonstrated in the test method described by Janssen et al., Arzneim.-Forsch. 10, 1003, (1960). For example compounds of formula I inhibit apomorphine (10 mg/kg s.c.) induced stereotyped gnawing in rats at dosages of from 0.03 to 0.32 mg/kg s.c.

Furthermore compounds of formula Ia and compounds of formula Ib, wherein $R_2'$ is methyl possess prolactin (PRL) secretion inhibiting activity as demonstrated e.g. by inhibition of basal prolactin secretion in male rats in the method described by Flückiger et al., Experientia 34, 1330 (1978). For example the compounds of formula Ia and the compounds of formula Ib, wherein $R_2'$ is methyl, exhibit activity in this test method at dosages of from 0.001 to 0.1 mg/kg s.c.

As will be appreciated, activity as PRL secretion inhibitors as demonstrable in the relevant test method described above is also demonstrative of dopamine agonist activity. Furthermore apomorphine antagonist activity as demonstrable in the relevant test method described above is also demonstrable of dopamine antagonist activity. Thus the compounds of formula Ia and compounds of formula Ib, wherein $R_2'$ is methyl, may be characterised as having a dual dopamine agonist/antagonist activity profile.

In view of their apomorphine antagonistic activity compounds of formula I, in particular compounds of formula Ib, are useful as neuroleptic agents, for example for the treatment of schizophrenia.

In view of their PRL secretion inhibiting activity compounds of formula Ia and compounds of formula Ib, wherein $R_2'$ is methyl, are useful as PRL secretion inhibitors, e.g. in the treatment of conditions or disorders for which reduction of prolactin levels is indicated, for example for the treatment of prolactin-dependent menstrual disorders including amenorrhea, for the inhibition of lactation including post-partum lactation and morbid lactation as well as for the treatment of hyperprolactinaemic hypogonadism in males and females and of prolactinoma. Furthermore more in view of concomitant dopamine agonist activity compounds of formula Ia and compounds of formula Ib, wherein $R_2'$ is methyl, are also useful as dopamine agonists, e.g. for the treatment of Morbus Parkinson.

It will be appreciated that where PRL inhibiting activity is accompanied by apomorphine antagonistic activity, e.g. as in the case of compounds of formula Ia and compounds of formula Ib, wherein $R_2'$ is methyl, in view of their dual dopamine agonistic/antagonistic properties the subject compounds will produce less side effects, e.g. only weak or no emetic activity occuring at endocrinologically active dosage.

For the above uses, the dosage required will of course vary depending on e.g. the particular compound employed, the mode of administration, the particular condition to be treated and the effect desired. In general, satisfactory results are obtained when administered at a daily dosage of about 0.01 to about 0.5 mg/kg animal body weight for apomorphine antagonistic activity and from about 0.01 to about 0.1 mg/kg animal body weight for PRL secretion inhibiting activity. For the larger mammals an indicated daily dosage is in the range from about 1 to about 40 mg of the compound for apomorphine antagonistic activity or from about 0.1 to about 10 mg for PRL secretion inhibiting activity respectively conveniently administered in divided doses 2 to 4 times a day in unit dosage form or in sustained release form. Suitable unit dosage forms accordingly comprise: from about 0.25 to about 20 mg and from about 0.025 to about 5 mg (according to intended utility) of the compound together with a pharmaceutically acceptable diluent or carrier.

The compounds of the invention may be administered in similar manner to known standards for use in the recited indications.

As previously indicated a suitable daily dosage for any particular compound will depend on a number of factors including its relative potency of activity.

Thus for the compound of Example 1 a determined $ED_{50}$ for apomorphine antagonistic activity in the above cited test method is 0.03 mg/kg s.c. compared with a measured $ED_{50}$ of 0.32 mg/kg s.c. for the known neuroleptic Haloperidol. Indicated dosages of compound pound 1 for use in the neuroleptic indication will accordingly be of the order of ca. 1/10 of those commonly employed using Haloperidol as drug substance.

For the compound of Example 1, a determined $ID_{50}$ for PRL secretion inhibiting activity in the above cited test method is 0.005 mg/kg s.c. compared with a measured $ID_{50}$ of 0.007 mg/kg s.c. for the known PRL secretion inhibitor Bromocriptine. It is therefore indicated that the compound may be administered at similar or lower dosages than conventionally employed for Bromocriptine.

The Example 1 compound is the preferred compound.

The compounds of formula I may be administered in free base form or in pharmaceutically acceptable acid addition salt form. Such salts may be prepared in conventional manner and exhibit the same order of activity as the free base form. The present invention also provides a pharmaceutical composition comprising a compound of formula I in free base form or in salt form in associatior with a pharmaceutically acceptable diluent or carrier. Such compositions may be formulated in conventional manner. The compounds may be administered by any conventional route in particular enterally preferably orally e.g. in the form of tablets or capsules, or parenterally e.g. in form of injectatle solutions or suspensions.

In accordance with the foregoing the present invention also provides a compound of formula I as hereinbefore defined for use as a pharmaceutical, i.e. for use in therapy, for example: for use as an apomorphine antagonist; or in particular in the case of compounds of formula Ia and compounds of formula Ib, wherein $R_2'$ is methyl as hereinbefore defined for use as an PRL secretion inhibitor or for use as a dopamine agonist; and especially for use in any of the specific indications hereinbefore recited in relation to such use; as well as a method of 1. effecting neuroleptic treatment,
2. inhibiting PRL secretion or
3. treating Morbus Parkinson e.g. for treating any of specific conditions hereinbefore recited in relation to such treatment, in a subject in need of such treatment, which method comprises administering to said subject an effective amount of a compound of formula I as hereinbefore defined, or in the case of a method as defined under 2 and 3 a compound of formula Ia and compounds of formula Ib, wherein $R_2'$ is methyl as hereinbefore defined or a pharmaceutically acceptable acid addition salt thereof.

EXAMPLES 5 and 6 in manner analogous to Example 1 there are prepared:

(a) 8α-(adamantyl-1-carbonyl)amino-2,6-dimethyl-9,10-didehyro-ergoline melting point 151° with foaming.

(b) 8α-(2,2-diethyl-butyryl)-amino-2,6-dimethyl-9,10-didenydro-ertoline (amorphous).

I claim:

1. A compound which is 2,6-dimethyl-8α-pivaloylamino-9,10-didehydro-ergoline or a pharmaceutically acceptable acid addition salt thereof.

2. A pharmaceutical composition useful for neuroleptic treatment, inhibiting PRL secretion or treating Morbus Parkinson which comprises an effective amount of a compound of claim 1 or a pharmaceutically acceptable acid addition salt thereof in association with a pharmaceutical carrier or diluent.

3. A method of effecting neuroleptic treatment which comprises administering a therapeutically effective amount of a compound of claim 1 or a pharmaceutically acceptable acid addition salt thereof to a subject in need of such treatment.

4. A method of inhibiting PRL secretion or treating Morbus Parkinson which comprises administering a therapeutically effective amount of a compound of claim 1 or a pharmaceutically acceptable acid addition salt thereof to a subject in need of such treatment.

* * * * *